United States Patent [19]

Saito et al.

[11] Patent Number: 4,992,551

[45] Date of Patent: Feb. 12, 1991

[54] DC-52 DERIVATIVES

[75] Inventors: Hiromitsu Saito, Sagamihara; Akira Sato, Machida; Masaji Kasai, Fujisawa; Makoto Morimoto, Shizuoka; Tadashi Ashizawa, Numazu, all of Japan

[73] Assignee: Kyowa Hakko Kogyo Co., Ltd., Tokyo, Japan

[21] Appl. No.: 435,246

[22] Filed: Nov. 13, 1989

[30] Foreign Application Priority Data

Nov. 16, 1988 [JP] Japan .................. 63-289565

[51] Int. Cl.$^5$ .................. A61K 31/495; C07D 498/22; C07D 471/18; C07B 37/10
[52] U.S. Cl. .................... 544/342; 544/338
[58] Field of Search ......................... 544/342

[56] References Cited

U.S. PATENT DOCUMENTS 4,650,869 3/1987 Hirata .................. 544/343
4,822,882 4/1989 Saito .................. 544/352
4,946,957 8/1990 Saito .................. 544/352

FOREIGN PATENT DOCUMENTS 0262984 4/1988 European Pat. Off.
63-88183 4/1988 Japan .
63-183583 7/1988 Japan .

OTHER PUBLICATIONS

Translation of Claims of JP 57-170189.

Primary Examiner—Mark L. Berch
Attorney, Agent, or Firm—Fitzpatrick, Cella, Harper & Scinto

[57] ABSTRACT

Disclosed are DC-52 derivatives represented by the formula:

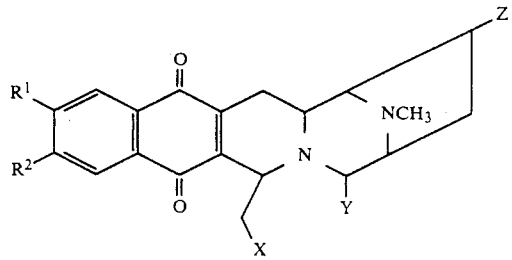

wherein each of $R^1$ and $R^2$ independently represents hydrogen or hydroxyl, X represents hydroxyl and Y represents cyano and Z represents carboxyl or hydroxymethyl, or pharmacologically acceptable salts thereof. The DC-52 derivatives are useful as antitumor agents.

1 Claim, No Drawings

DC-52 DERIVATIVES

BACKGROUND OF THE INVENTION

The present invention relates to DC-52 derivatives.

DC-52 derivatives have an antitumor activity and are useful as antitumor agent.

JP-A-170189/1982 discloses DC-52, which is a compound represented by the formula:

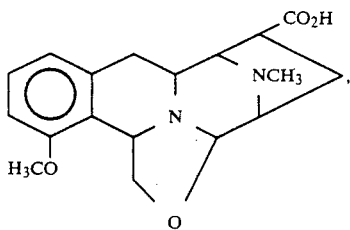

and exhibits an antitumor activity against lymphocytic leukemia P388, etc. in addition to an antibacterial activity against various bacteria.

U.S. Pat. No. 4,650,869 (JP-A-210086/1984) discloses DX-52-1, a derivative of DC-52, having an antitumor activity and represented by the formula:

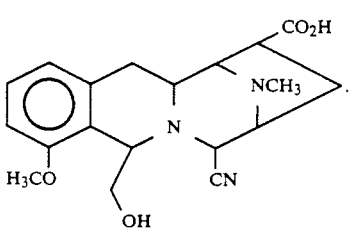

EP-A-283521 (JP-A-88183/1988) discloses a derivative represented by the formula:

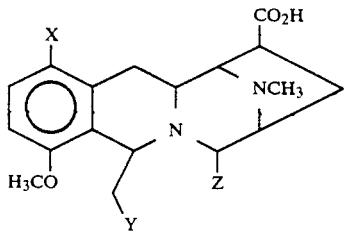

wherein X represents chlorine, bromine, iodine, hydroxyl, formyl, hydroxyiminomethyl, cyano, nitro, amino or lower alkanoylamino, Y represents hydroxyl and Z represents cyano, or Y and Z are combined together to represent —O— as —Y—Z—. JP-A-183583/88 discloses a derivative represented by the formula:

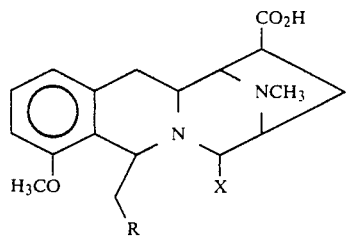

wherein R represents hydrogen, alkanoyloxy having 1 to 18 carbon atoms, oleoyloxy, linoloyloxy, linolenoyloxy, retinoyloxy, unsubstitued or substitued benzoyloxy in which the substituent is halogen or lower alkoxy, mercapto, alkanoylthio having 1 to 18 carbon atoms, oleoylthio, linoloylthio, linolenoylthio, retinoylthio, unsubstituted or substituted benzoylthio in which the substituent is halogen or lower alkoxy, azido, amino, —NHZ [in which Z is an α-amino acid residue (wherein the OH of carboxyl of the α-amino acid is removed and the amino and/or carboxyl when it is present may be protected by their protective groups conventionally used in the peptide synthetic chemistry), pyruvoyl, citroyl or acetyl], cyano or halogen, and X represents cyano or hydroxyl. EP-A-262984 discloses a compound represented by the formula:

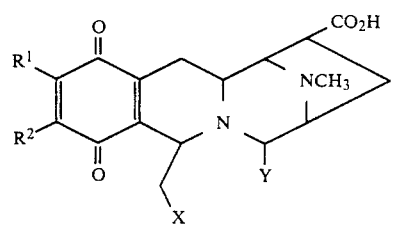

wherein each of $R^1$ and $R^2$ independently represents hydrogen, lower alkoxy, azido, amino, lower alkylamino, dilower alkylamino, cyclic amino, lower alkylthio, or unsubstituted or substituted arylthio, X represents hydroxyl and Y represents cyano, or X and Y are combined together to represent —O— as —X—Y—.

SUMMARY OF THE INVENTION

The object of the present invention is to provide a DC-52 derivative having superior properties over the prior art compounds.

In accordance with the present invention, there is provided DC-52 derivatives represented by the formula (I):

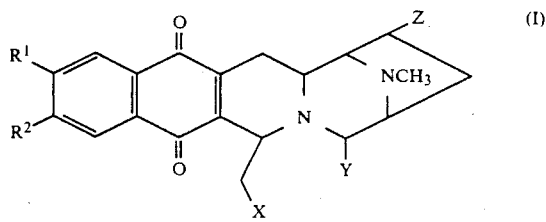

wherein each of $R^1$ and $R^2$ independently represents hydrogen or hydroxyl, X represents hydroxyl and Y represents cyano, or X and Y are combined together to represent —O— as —X—Y—and Z represents carboxyl or hydroxymethyl (hereinafter referred to as compounds I and Compounds of other formulae are similarly designated) and pharmacologically acceptable salts thereof.

DETAILED DESCRIPTION OF THE INVENTION

Pharmacologically acceptable salts of compounds I include pharmacologically acceptable acid addition salts, alkali metal salts, alkaline earth metal salts and ammonium salts and pharmacologically acceptable organic base addition salts. Pharmacologically acceptable acid addition salts include pharmacologically acceptable inorganic acid addition salts such as hydrochloride, hydrobromide, hydroiodide, sulfate, phosphate and nitrate; and pharmacologically acceptable organic acid addition salts such as acetate, benzoate, maleate, fumarate, succinate, tartrate, citrate, oxalate, glyoxylate, aspartate, methansulfonate, ethanesulfonate, propanesulfonate, methanesulfonate, ethanedisulfonate, α, β-ethanedisulfonate and benzenesulfonate. Alkali metal salts include sodium salt, potassium salt, etc. and alkaline earth metal salts include calcium salt, magnesium salt, etc. Pharmacologically acceptable organic base addition salts include addition salts of ethanolamine, triethylamine, morpholine, piperidine, etc.

A process of preparing compounds I is described below.

Compounds I can be prepared according to the following steps:

Step 1

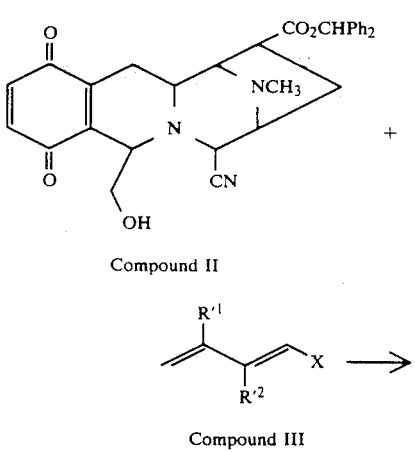

Compound II

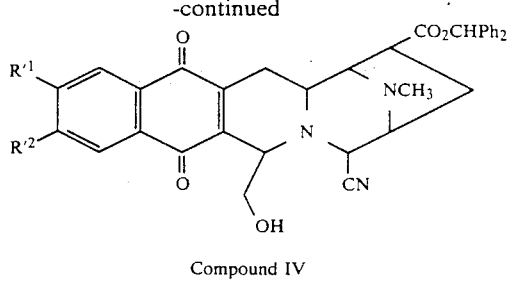

Compound IV

Wherein Ph represents phenyl, each of R'1 and R'2 independently represents hydrogen or trimethylsiloxy, and X represents acetoxy, methoxy or trimethylsiloxy.

Compounds II as starting compounds are known and disclosed in EP-A-262984, and compounds III are commercially available or can be synthesized in a known process. A compound IV can be obtained by reacting a compound II with a compound III in an inert solvent.

As inert solvents, are usable benzene, toluene, xylene, etc. A compound III is used in an amount of 1 to 3 molar equivalents based on a compound II. The reaction is carried out at 50° to 130° C. and completed in 5 hours to 2 days.

Step 2

Compound IV wherein R'1 and R'2 represent trimethylsiloxy; or one of R'1 and R'2 represents trimethylsiloxy and the other represents hydrogen. Such combination is referred to as "R'1 and/or R'2 represent trimethylsiloxy". Similar definitions are applied hereinafter

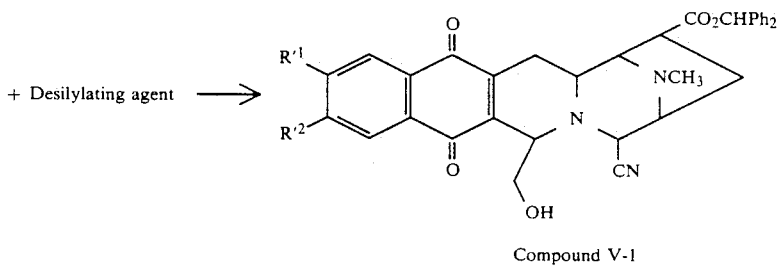

Compound V-1

Wherein R'1 and/or R'2 are hydroxyl.

A compound V-1 can be obtained by reacting a compound IV with a desilylating agent in an inert solvent.

As inert solvents, are usable methanol, ethanol, tetrahydrofuran, dioxane, acetonitrile, water, etc.

As desilylating agents, are usable potassium carbonate, tetra-n-butylammonium fluoride, etc. A desilylating agent is used in an amount of 1 to 10 molar equivalents based on a compound IV. The reaction is carried out at 0° to 60° C. and completed in 1 to 15 hours.

Step 3

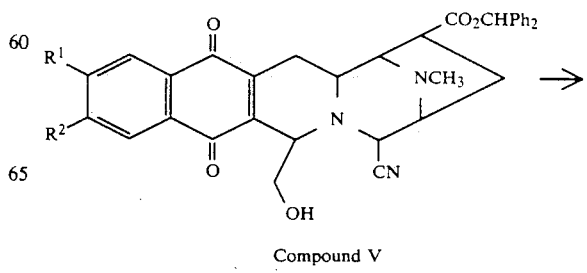

Compound V

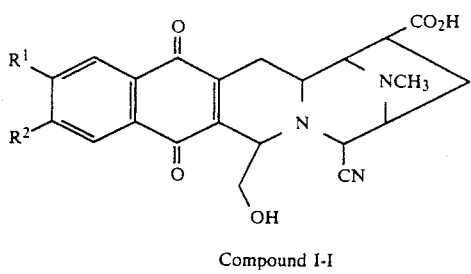

Compound I-1

Wherein Compound V mean compounds IV wherein R'¹ and
R'² are hydrogen and compounds V-1; and ph, R¹ and R² are as hereinbefore defined.

A compound I-1 can be obtained by reacting a compound V with trifluoroacetic acid in an inert solvent.

As inert solvents are usable methylene chloride, dichloroethane, chloroform, etc. Trifluoroacetic acid is used in an amount of 5 molar equivalents to large excess based on a compound V. The reaction is carried out at 0° to 50° C. and completed in 1 to 10 hours.

Step 4

Compound V →

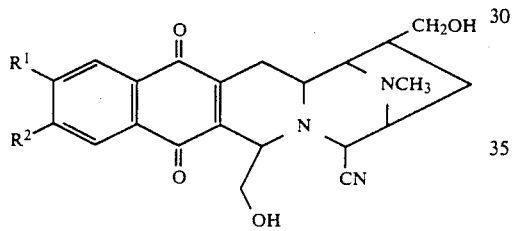

Compound I-2

Wherein R¹ and R² are as hereinbefore defined.

A compound I-2 can be obtained by reducing a benzhydryl ester of a compound V in an inert solvent.

As inert solvents are usable tetrahydrofuran, diethyl ether, toluene, benzene, methanol, ethanol, etc.

$LiAlH_4$, $LiBH_4$, $NaBH_4$, etc. can be used as reducing agents and are usually used in an amount of 3 to 10 molar equivalents based on a compound V. The reaction is carried out at −10° to 70° C. and completed in 1 to 10 hours.

Step 5

Compound I-1 or compound I-2 →

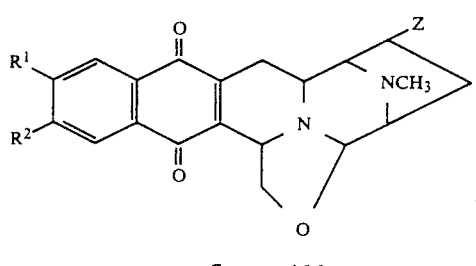

Compound I-3

Wherein R¹, R² and Z are as hereinbefore defined.

A compound I-3 can be obtained by reducing a compound I-1 or compound I-2 with a silver salt in an inert solvent.

As inert solvents are usable acetonitrile, methanol, ethanol, tetrahydrofuran, dioxane, etc. As silver salts are usable silver nitrate, silver chlorate, silver perchlorate, silver fluoride, etc. A silver salt is used in an amount of 1 to 5 molar equivalents based on a compound I-1 or compound I-2. The reaction is usually carried out at 0° to 50° C. and completed in 30 minutes to 5 hours.

After completion of the reaction of each step, the reaction is stopped by adding an acid, water, a buffer or the like, if necessary, and the mixture is concentrated as such or after extraction with a nonaqueous solvent such as ethyl acetate, chloroform, etc. Alternatively, the reaction mixture is concentrated as such and purified. The purification can be carried out by column chromatography, thin layer chromatography, preparative high performance liquid chromatography, recrystallization or the like.

Compounds I and pharmacologically acceptable salts thereof have a strong antitumor activity against lymphocytic leukemia P-388, etc.

Structures of typical compounds I and compound numbers are listed in Table 1.

TABLE 1

| Compound No. | $R_1$ | $R_2$ | X | Y | Z |
|---|---|---|---|---|---|
| 1 | H | H | OH | CN | $CO_2Na$ |
| 2 | H | H | —O— | | $CO_2H$ |
| 3 | H | H | OH | CN | $CH_2OH$ |
| 4 | H | H | —O— | | $CH_2OH$ |
| 5 | OH or H | H or OH | OH | CN | $CO_2H$ |
| 6 | OH or H | H or OH | —O— | | $CO_2H$ |

Antitumor activities of compounds I are demonstrated below by an experimental example.

Experimental example

Lymphocytic leukemia P-388 tumor cells ($1 \times 10^6$) were intraperitoneally implanted into CDF male mice weighing about 22g, one group consisting of 5 animals. 24 hours after the implantation was intraperitoneally administered once 0.2 ml of a solution of each drug in phosphate-buffered physiological saline. The life prolonging effect of the drugs was shown in T/C. The results are shown in Table 2.

TABLE 2

| Compound | Dose (mg/kg) | T/C (%)* |
|---|---|---|
| 1 | 25 | 126 |

TABLE 2-continued

| Compound | Dose (mg/kg) | T/C (%)* |
|---|---|---|
| 2 | 25 | 158 |

*T/C (%) = $\frac{\text{Average survival days in each test example}}{\text{Average survival days in control}} \times 100$ Examples and reference examples are illustrated below.

Physicochemical data exhibited in the following examples and reference examples were measured by the following instruments:
NMR Bruker AM400 (400 MHz).
MS Hitachi B-80.

EXAMPLE 1

Synthesis of compound 1

In this example, 1.89 g of compound a obtained in Reference example 1 was dissolved in 50 ml of methylene chloride. Then, 3.5 ml of anisole and 6 ml of trifluoroacetic acid (TFA) were added thereto, and the mixture was stirred at room temperature for one hour and 30 minutes. After the reaction solution was concentrated, the concentrate was dissolved in a sodium bicarbonate solution and purified by column chromatography (Diaion HP-20 180 ml, eluting solvent; water : methanol = 1 : 0 to 4 : 1 v/v) to obtain 1.12 g (79.2%) of compound 1.

$^1$H-NMR (DMSO-$d_6$ - CD$_3$OD) ppm; 8.11-8.14 (m, 2H), 7.87-7.92 (m, 2H), 4.66 (d, 1H, J=2.5 Hz), 4.09 (m, 1H), 4.02 (m, 1H), 3.96 (bs, 1H), 3.90 (dd, 1H, J=11.4, 2.3 Hz), 3.68 (dd, 1H, J=11.4, 4.1 Hz), 3.51 (dd, 1H, J=9.9, 5.7 Hz), 3.07 (bd, 1H, J=11.2 Hz), 3.02 (dd, 1H, J=17.3, 2.5 Hz), 2.70 (dt, 1H J=13.4, 6.3 Hz), 2.62 (s, 3H), 2.36 (ddd, 1H, J=17.2, 10.8, 2.4 Hz), 2.28 (dd, 1H, J=13.7, 10.0 Hz).

SIMS (m/z); 410 (M+3)$^+$(carboxylic acid-free).

EXAMPLE 2

Synthesis of compound 2

In this example, 900 mg of compound 1 was dissolved in a mixture of 15 ml of acetonitrile and 15 ml of methanol. Then, 1.07 g of silver nitrate was added thereto, and the mixture was stirred at room temperature for 2 hours and 30 minutes. Then, 1N hydrochloric acid was added thereto. After removal of the formed precipitate by filtration acetonitrile and methanol were distilled away. The resulting concentrate was purified by column chromatography (Diaion HP-20 100 ml, eluting solvent; water : methanol = 1 : 0 to 3 : 2 v/v) to obtain 719 mg (90.2%) of compound 2.

$^1$H-NMR (D$_2$O) ppm; 7.98 (m, 2H), 7.79 (m, 2H), 5.00 (d, 1H, J=3.3 Hz), 4.34 (m, 1H), 4.29 (s, 1H), 4.05 (m, 1H), 3.87 (dd, 1H, J=12.0, 2.7 Hz), 3.69 (dd, 1H, J=12.0, 3.3 Hz), 3.48 (bd, 1H, J=10.7 Hz), 3.42 (bd, 1H, J=10.6, 5.4 Hz), 2.95 (m, 1H), 2.84 (s, 3H), 2.58 (m, 1H), 2.41 (dd, 1H, J=14.3, 10.6 Hz), 2.29 (m, 1H).

SIMS (m/z); 383 (M+3)$^+$.

EXAMPLE 3

Synthesis of compound 3

In this example, 40 mg of LiAlH$_4$ was suspended in 3 ml of tetrahydrofuran (THF) in an argon gas atmosphere. Under cooling to 0° C. was dropwise added a solution of 180 mg of compound a obtained in Reference example 1 in 4 ml of THF. After stirring at 0° C. for 50 minutes, 10 mg of LiAlH$_4$ was added, followed by stirring for further 2 hours and 15 minutes. After stirring for 30 minutes after addition of ethyl acetate and an acetate buffer (pH 4.0), a NaHCO$_3$ solution was added, and the mixture was extracted three times with ethyl acetate. The extract was washed with saturated aqueous sodium chloride, dried over anhydrous sodium sulfate, and evaporated to remove the solvent. The residue was purified by column chromatography (Wako gel C-200 20 ml, eluting solvent; n-hexane : ethyl acetate = 1 : 1 to 1 : 2 v/v) to obtain 39.9 mg (32.3%) of compound 3.

$^1$H-NMR (CDCl$_3$-CD$_3$OD) ppm; 8.08 - 8.10 (m, 2H), 7.74 7.76 (m, 2H), 4.18 (m, 1H), 4.13 (bs, 1H), 3.87 (dd, 1H, J=11.6, 2.8 Hz), 3.70 (dd, 1H, J=11.6, 3.8 Hz), 3.62-3.66 (m, 2H), 3.15 (br, 1H), 3.03 (m, 1H), 2.89 (dd, 1H, J=17.7, 2.2 Hz), 2.64 (bs, 3H), 2.56 (m, 1H), 2.24 (ddd, 1H, J=17.7, 11.0, 2.6Hz), 1.91 -2.03 (m, 2H).

SIMS (m/z); 396 (M+3)$^+$.

EXAMPLE 4

Synthesis of compound 4

In this example, 145 mg of compound 3 was dissolved in 3 ml of acetonitrile and 1 ml of methanol. Then, 157 mg of silver nitrate was added thereto. After stirring at room temperature for 4 hours and 50 minutes, the insoluble matter was removed by filtration and the filtrate was concentrated. The concentrate was purified by column chromatography (Diaion HP-20 15 ml, eluting solvent, water : methanol = 1 : 0 to 4 : 1 v/v) to obtain 90.2 mg (66.8%) of compound 4.

$^1$H-NMR (CO$_3$OD) ppm; 8.07-8.09 (m, 2H), 7.78-7.81 (m, 2H), 4.61 (d, 1H, J=3.1 Hz), 4.41 (m, 1H), 4.20 (m, 1H), 3.89 (dd, 1H, J=11.6, 2.7 Hz), 3.87 (bs, 1H), 3.73 (dd, 1H, J=11.2, 6.0 Hz), 3.61-3.68 (m, 2H), 3.40 (m, 1H), 2.97 (s, 3H), 2.94 (dd, 1H, J=17.3, 2.5 Hz), 2.32 (dd, 1H, J=14.1, 9.9 Hz), 2.28 (ddd, 1H, J=17.2, 11.2, 2.3 Hz), 2.08 (m, 1H).

SIMS (m/z); 369 (M+3)$^+$.

EXAMPLE 5

Synthesis of compound 5

In the example, 335 mg of compound b obtained in Reference example 2 was dissolved in 7 ml of methylene chloride. Then, 0.5 ml of anisole and 1 ml of TFA were added thereto. The mixture was stirred at room temperature for 2 hours. The reaction solution was concentrated and the residue was purified by column chromatography (Diaion HP-20 40 ml, eluting solvent; water : methanol = 1 : 0 to 1 : 1 v/v) to obtain 234 mg (97.3%) of compound 5.

$^1$H-NMR (DMSO-$d_6$) ppm; 12.34 (br, 1H), 10.92 (s, 1H), 7.89 (d, 1H, J=8.5 Hz), 7.31 (d, 1H, J=2.6 Hz), 7.15 (dd, 1H, J=8.5, 2.6 Hz), 4.63 (br, 1H), 4.32 (bs, 1H), 3.82 (bs, 1H), 3.71 (dd, 1H, J=11.2, 1.9 Hz), 3.43-3.48 (m, 2H), 3.15 (m, 1H), 2.67-2.75 (m, 2H), 2.40 (m, 1H), 2.22 (s, 3H), 2.12 (ddd, 1H, J=16.7, 10.5, 2.2 Hz), 1.91 (m, 1H).

SIMS (m/z); 426 (M+3)$^+$; 425 (M+2)$^+$, 424 (M+1)$^+$.

EXAMPLE 6

Synthesis of compound 6

In this example, 209 mg of compound 5 was dissolved in a mixture of 3 ml of acetonitrile and 6 ml of methanol. Then, 250 mg of silver nitrate was added thereto. After stirring at room temperature for 3 hours, water was added, the insoluble matter was removed by filtration, and acetonitrile and methanol were distilled away from the filtrate. The residue was purified by column chromatography (Diaion HP-20 30 ml, eluting solvent; water : methanol = 1 : 0 to 1 : 1 v/v) to obtain 185 mg (94.6%) of compound 6.

¹H-NMR (DMSO-d$_6$) ppm; 7.83 (d, 1H, J=8.5 Hz), 7.29 (d, 1H, J=2.5 Hz), 7.13 (dd, 1H, J=8.5, 2.5 Hz), 4.38 (t, 1H, J=6.9 Hz), 3.95 (d, 1H, J=2.5 Hz), 3.57 (m, 1H), 3.41 (s, 1H), 3.26-3.40 (2H, overlapping with absorption of water), 3.06 (m, 1H), 2.83 (dd, 1H, J=9.7, 5.4 Hz), 2.72 (ddd, 1H, J=20.3, 5.8, 3.2 Hz), 2.39 (ddd, 1H, J=20.2, 8.2, 3.3 Hz), 2.30 (s, 3H), 2.17 (dt, 1H, J=12.5, 6.1 Hz), 1.78 (dd, 1H, J=12.7, 9.8 Hz).

SIMS (m/z); 399 (M+3)⁺.

Structures of compounds obtained by the following reference examples and compound numbers are indicated below:

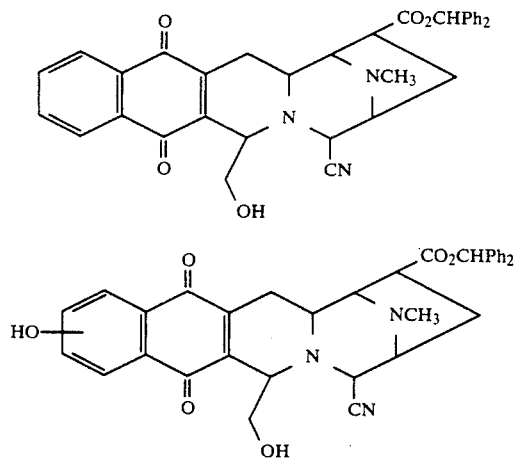

REFERENCE EXAMPLE 1

Synthesis of compound a

In this reference example, 1.0 g of compound II was dissolved in 25 ml of benzene. Then, 0.27 ml of 1-acetoxy-1,3-butadiene was added thereto. The mixture was sealed in a pressure vessel and stirred at 90° C. for 19 hours. The reaction solution was concentrated and purified by column chromatography (Wako gel C-200 100 ml, eluting solvent; chloroform) to obtain 849 mg (77.5%) of compound a.

¹H-NMR (CDCl$_3$) ppm; 8.08-8.11 (m, 2H), 7.72-7.76 (m, 2H), 7.30-7.40 (m, 10H), 6.92 (s, 1H), 4.16 (m, 1H), 4.04 (d, 1H, J=2.9 Hz), 3.88 (dd, 1H, J=11.7, 3.2 Hz), 3.76 (dd, 1H, J=11.8, 2.4 Hz), 3.57 (bs, 1H), 3.52 (m, 1H), 3.16 (dd, 1H, J=9.6, 5.7 Hz), 3.05 (m, 1H), 3.01 (m, 1H), 2.71 (m, 1H), 2.28 (ddd, 1H, J=18.9, 12.0, 2.7 Hz), 2.18 (s, 3H), 1.98 (dd, 1H, J=13.6, 9.6 Hz).

EIMS (m/z); 573(M⁺), 546, 542, 501, 374, 167.

REFERENCE EXAMPLE 2

Synthesis of compound b

In this reference example, 500 mg of compound II was dissolved in 15 ml of benzene. Then, 0.22 ml of 1-methoxy-3-trimethylsiloxy-1,3-butadiene was added thereto. The mixture was sealed in a pressure vessel and stirred at 90° C. for 25 hours. After distilling away the benzene, the residue was dissolved in 20 ml of methanol, 7.5 mg of potassium carbonate was added, and the mixture was stirred at room temperature for 3 hours and 30 minutes. After distilling away methanol, the residue was distributed between water and ethyl acetate. The ethyl acetate layer was separated, washed with saturated aqueous sodium chloride, dried over anhydrous sodium sulfate and evaporated to remove the solvent. The residue was purified by column chromatography (Wako gel C-200 80 ml, eluting solvent; chloroform : methanol = 1 : 0 to 100 : 1 v/v) to obtain 358 mg (62.0%) of compound b.

¹H-NMR (CD$_3$Cl$_3$) ppm; 7.75 (br, 1H), 7.23-7.40 (m, 12H), 6.91 (s, 1H), 4.06 (br, 1H), 4.01 (bs, 1H), 3.73-3.82 (m, 2H), 3.59 (s, 1H), 3.48 (m, 1H), 3.22 (m, 1H), 2.98 (m, 1H), 2.87 (m, 1H), 2.68 (m, 1H), 2.16 (s, 3H), 2.12-2.24 (m, 1H), 2.00 (m, 1H).

SIMS (m/z): 592 (M+3)⁺, 565.

What is claimed is:

1. A DC-52 Derivative represented by the formula:

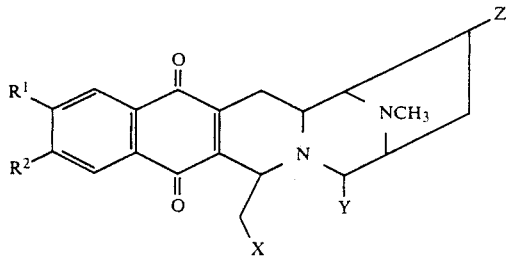

wherein each of R¹ and R² independently represents hydrogen or hydroxyl, X represents hydroxyl and Y represents cyano and Z represents carboxyl or hydroxymethyl, or pharmacologically acceptable salts thereof.

* * * * *